US00PP15638P3

(12) United States Plant Patent
Coiner

(10) Patent No.: US PP15,638 P3
(45) Date of Patent: Mar. 8, 2005

(54) HYBRID TEA ROSE PLANT NAMED 'FRIVOLOUS PINK'

(50) Latin Name: *Rosa hydrida*
Varietal Denomination: Frivolous Pink

(75) Inventor: James W. Coiner, La Verne, CA (US)

(73) Assignee: Coiner Nursery, LaVerne, CA (US)

( * ) Notice: Subject to any disclaimer, the term of this patent is extended or adjusted under 35 U.S.C. 154(b) by 0 days.

(21) Appl. No.: 10/016,068

(22) Filed: Dec. 5, 2001

(65) Prior Publication Data

US 2003/0106113 P1 Jun. 5, 2003

(51) Int. Cl.[7] ..... A01H 5/00
(52) U.S. Cl. ..... Plt./137
(58) Field of Search ..... Plt./130, 132, 137, Plt./138, 148

*Primary Examiner*—Howard J. Locker
(74) *Attorney, Agent, or Firm*—Christie, Parker & Hale, LLP

(57) ABSTRACT

A new and distinct Hybrid Tea Rose plant variety with pink flowers.

2 Drawing Sheets

Classification: The present invention relates to a new *Rosa hybrida* plant.

Variety denomination: The new plant has the varietal denomination 'Frivolous Pink'.

BACKGROUND OF THE INVENTION

The present invention relates to a new and distinct variety of rose plant of the hybrid tea rose of the genus *Rosaceae* which was created by crossing as seed and pollen parents two (2) unknown rose varieties. The varietal denomination of the new variety is 'Frivolous Pink'.

SUMMARY OF THE INVENTION

Among the novel characteristics possessed by this new variety which distinguishes it from other varieties of which I am aware, is its pink flowers.

Asexual reproduction by propagation by budding of the new variety as performed in Wasco, Calif. shows that the foregoing and other distinguishing characteristics come true to form and are established and transmitted through succeeding propagations.

BRIEF DESCRIPTION OF THE ILLUSTRATIONS

The accompanying illustrations show typical specimens of the flowers and foliage of the new variety depicted in color as nearly true as it is reasonably possible to make same in color illustrations of this character.

DESCRIPTION OF THE NEW VARIETY

Figure 1:
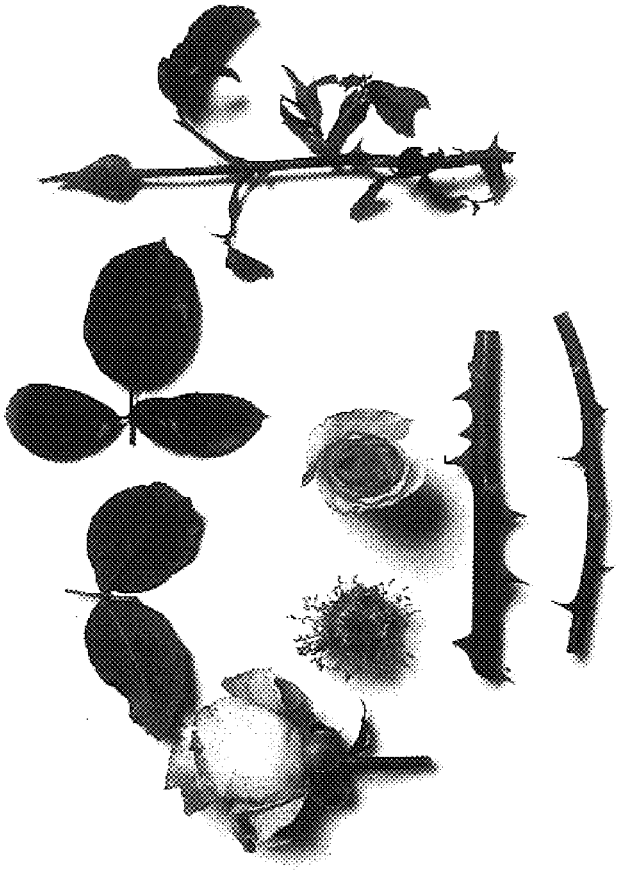
FIG. 1 shows a bud with flowering stem; portions of a flowering stem and main stem, foliage, bloom in early stages of opening, and reproductive organs.
Figure 2:
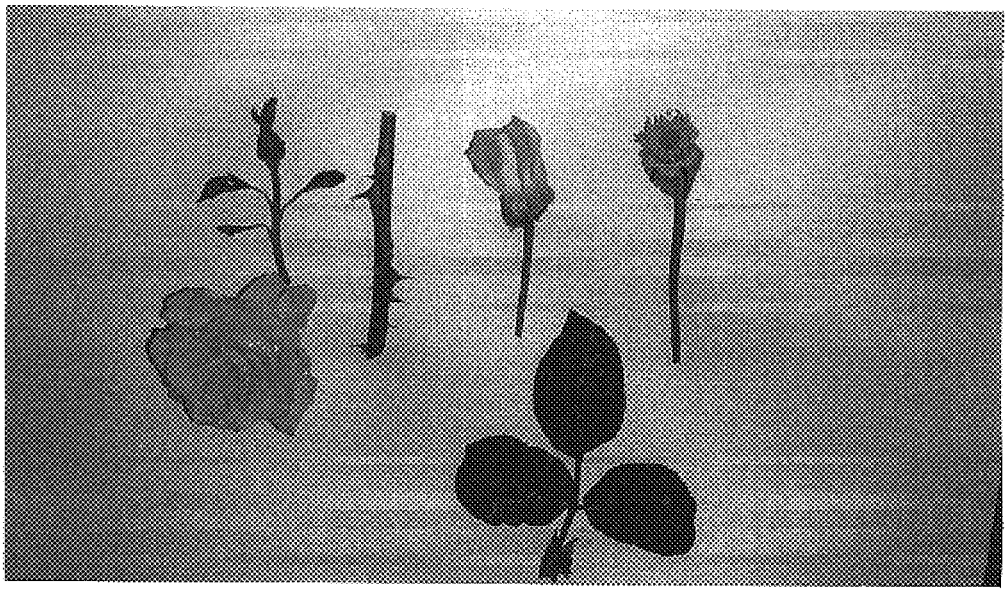
FIG. 2 shows foliage, bud with a portion of the flowering stem, a portion of a main stem, foliage with stipules, reproductive organs, and the bloom.

The following is a detailed description of 2-year budded plants of the new variety, with color terminology in accordance with The Royal Horticultural Society Colour Chart (R.H.S.C.C.). The terminology used in color description herein refers to plate numbers in the aforementioned color chart. Phenotypic expression may vary with light availability, environmental and cultural conditions.

The following observations are made of specimens grown outdoors in Wasco, Calif., during the month of November budded on 'Dr. Huey' understock.

PLANT

Form: Compact.
Growth: Medium.
Size: Height about 3½ feet; width about 2 feet.
Foliage:
- *Size.*—Terminal leaflet length about 2⁹⁄₁₆ inches; width about 1⅜ inches.
- *Quantity.*—Leaves compound, with 3 to 7 leaflets; most typically 7 leaflets.
- *Color.*—New foliage: Upper side near 175A; under side near 175C. Mature foliage: Upper side near 137A; under side near 137C.
- *Shape.*—Elliptic.
- *Texture.*—Upper side: Smooth, semi-glossy. Under side: Matte.
- *Edge.*—Serrated.
- *Serration.*—Slight.

Petioles: Top surface color near 143B; Under side near 144B.
Stipules: Normal.
Rachis: Few prickles.

WOOD

New shoots:
- *Bark.*—Smooth.
- *Wood.*—Near 143C.

Old wood:
- *Bark.*—Smooth.
- *Wood.*—Near 141C.

Flowering stem: Length about 16 inches.
Winter hardiness: Completely winter hardy.
Preferred growing conditions: Full sun.
Growth habit: Medium vigor.
Leaves per stem: About 5.

Prickles/thorns: The cultivar has an average number of thorns and prickles; thorns about 3/16 inch long, near 143C.

FLOWER/INFLORESCENCE

Blooming habit: Recurrent.
Bud: Length about 2 inches; width about 1¼ inches.
*Form.*—Classic rose.
*Color.*—Before sepals divide color near 56A; when sepals first divide color near 55B; when petals begin to unfurl color near 55C.
Sepals: Long, thin on ends, usually 5 sepals per bloom, multiple serrated extensions.
*Size.*—Length in relation to bud, about 1 3/16 inches.
*Color.*—Topside near 145A; bottom near 145B.
Peduncle:
*Length.*—About 2¾ inches, smooth.
*Strength.*—Erect.
*Color.*—Near 147B.
Flower:
*Size.*—About 4 inches.
*Borne.*—Multiple blooms in sprays, usually about 5 to 6 blooms per spray.
*Form.*—High centered, opens very flat with age.
Petalage: About 20, petals are fan-shaped.
*Petaloids in center.*—About 3.
Fragrance: Slight.
Lasting quality: About 2 weeks on plant; about 5 days after cutting.
Color:
*During first 2 days.*—Inner petals at flower center topside near 36A; bottom near 36C; outer petals topside near 36B, bottom near 4B, tips of petals are darker pink, near 39A, balance of petals are lighter near 36B.
Base of petals (point of attachment): Near 4B.
General tonality from a distance: Near 36A.
Color change: As bloom ages, fades to near 158C; after 3 or more days, fades to near 158C.
Petals:
*Texture.*—Soft.
*Shape.*—Oblong shape, length about 1½ inches; width about 1¼ inches.
*Arrangement.*—Imbricated.
*Appearance.*—Velvety.

REPRODUCTIVE ORGANS

Arrangement of stamens, filaments and anthers: Regularly arranged around styles.
Color: Filaments near 4B; Anthers near 4D.
Pollen: No pollen.
Styles: Medium length.
Hips/seed vessels/ovaries:
*Shape.*—Round.
*Size.*—About ½ inch.
*Color.*—Near 147B.
Seeds: No seeds.
Disease resistance: The cultivar exhibits an average resistance/susceptibility to disease.

I claim:

1. A new and distinct Hybrid Tea Rose plant of the variety substantially as shown and described.

* * * * *